United States Patent [19]

McGrady et al.

[11] Patent Number: 5,245,993
[45] Date of Patent: Sep. 21, 1993

[54] PILOT'S ENSEMBLE WITH INTEGRATED THREAT PROTECTION

[75] Inventors: Michael B. McGrady, Federal Way; Michael W. Wright, Renton, both of Wash.

[73] Assignee: The Boeing Company, Seattle, Wash.

[21] Appl. No.: 785,522

[22] Filed: Oct. 31, 1991

[51] Int. Cl.$^5$ .................. A62B 17/00; A62B 18/00
[52] U.S. Cl. .................. 128/201.22; 128/202.11; 128/206.23; 128/201.24; 2/69; 2/DIG. 1; 2/436; 2/205
[58] Field of Search .................. 128/201.22, 201.23, 128/201.24, 201.25, 201.29, 201.15, 202.11, 206.23, 206.24; 2/6, 426, 427, 428, 435, 436, 69, DIG. 1, 84, 202, 205

[56] References Cited

U.S. PATENT DOCUMENTS

| | | | |
|---|---|---|---|
| H823 | 10/1990 | Conkle et al. | 2/84 X |
| 1,915,818 | 6/1933 | DiCara | 128/201.22 |
| 1,931,562 | 10/1933 | Thompson . | |
| 2,222,971 | 11/1940 | Wright | 128/201.15 |
| 2,414,405 | 1/1947 | Bierman et al. | 128/201.23 X |
| 2,813,271 | 11/1957 | Finken | 2/6 |
| 2,871,849 | 2/1959 | Chatham et al. . | |
| 2,886,027 | 5/1959 | Henry . | |
| 3,049,896 | 8/1962 | Webb | 128/201.25 |
| 3,108,282 | 10/1963 | Rehman et al. | 2/6 |
| 3,284,805 | 11/1966 | Seeler . | |
| 3,463,150 | 8/1969 | Penfold | 128/202.11 |
| 3,505,990 | 4/1970 | Hawkins . | |
| 3,516,404 | 6/1970 | Spross . | |
| 3,667,460 | 6/1972 | Shepard | 128/201.15 |
| 3,751,727 | 8/1973 | Shepard et al. . | |
| 4,035,845 | 7/1977 | Hochwalt | 2/6 |
| 4,095,289 | 6/1978 | Kissen et al. | 3/6 X |
| 4,117,552 | 10/1978 | Simpson . | |
| 4,266,301 | 5/1981 | Canda | 2/6 X |
| 4,271,833 | 6/1981 | Moretti | 128/201.29 |
| 4,352,353 | 10/1982 | Bolton et al. . | |
| 4,468,101 | 8/1984 | Ellis . | |
| 4,633,526 | 1/1987 | Richardson . | |
| 4,676,236 | 6/1987 | Piorkowski et al. | 128/201.23 |
| 4,703,879 | 11/1987 | Kastendieck et al. . | |
| 4,734,939 | 4/1988 | Copp . | |
| 4,799,476 | 1/1989 | McGrady . | |
| 4,918,752 | 4/1990 | Briggs . | |
| 4,922,550 | 5/1990 | Verona et al. . | |
| 4,925,133 | 5/1990 | Wurst et al. . | |
| 5,014,355 | 5/1991 | Vollenweder | 2/DIG. 1 X |

Primary Examiner—V. Millin
Assistant Examiner—Sebastiano Passaniti
Attorney, Agent, or Firm—Joan H. Pauly

[57] ABSTRACT

A pilot's ensemble provides protection against cold water immersion and hostile threats, such as chemical and biological agents, while minimizing bulk and weight of the ensemble and impacts to and burdens on the pilot. The ensemble includes a garment (40) having an outer shell (14) impermeable to liquids and gases and a lining (58) bonded to an inner surface of a torso portion of the shell (14). Air is supplied to the lining (58) through a ventilation port (42) to control body temperature. Ensemble headgear includes a helmet (76) with upper and lower pairs of mounting members (78, 80, 82, 84). A permeable hood (70) is worn under the helmet (76) and has chemical vapor absorbing neck portions. A breathing mask (92) is removably attachable to the lower pair of mounting members (82, 84). Goggles (96) are removably attachable to the upper pair (78, 80). The goggles (96) seal the ocular cavity of the pilot and overlap the mask (92) and hood (70) to completely cover the pilot's face. A passageway (86) in the helmet (76) routes inflowing air to the goggles (96) to prevent fogging and maintain pressurization of the ocular cavity to prevent inboard leakage. Elements of the ensemble are selectively doffable in flight.

15 Claims, 7 Drawing Sheets

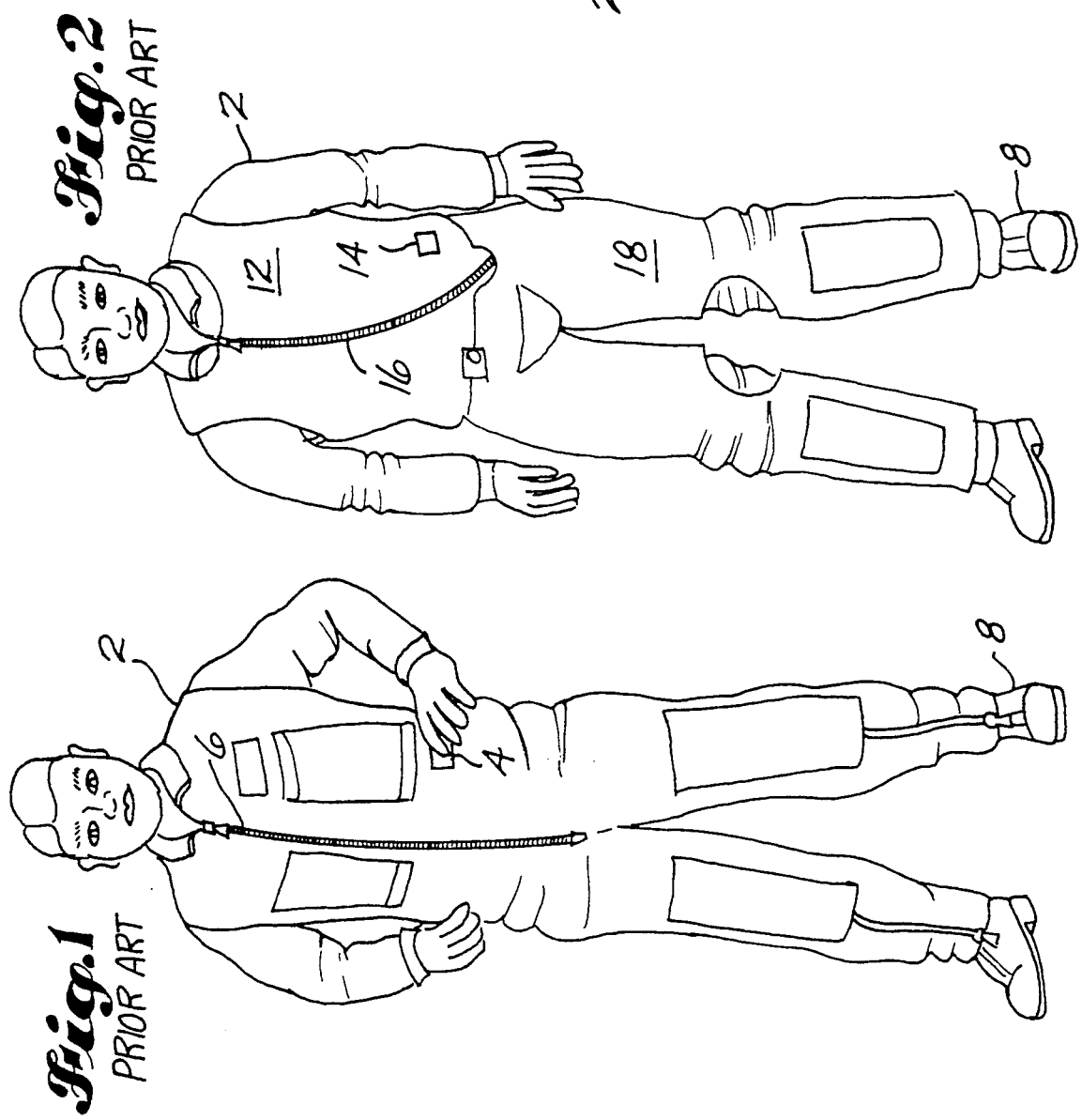

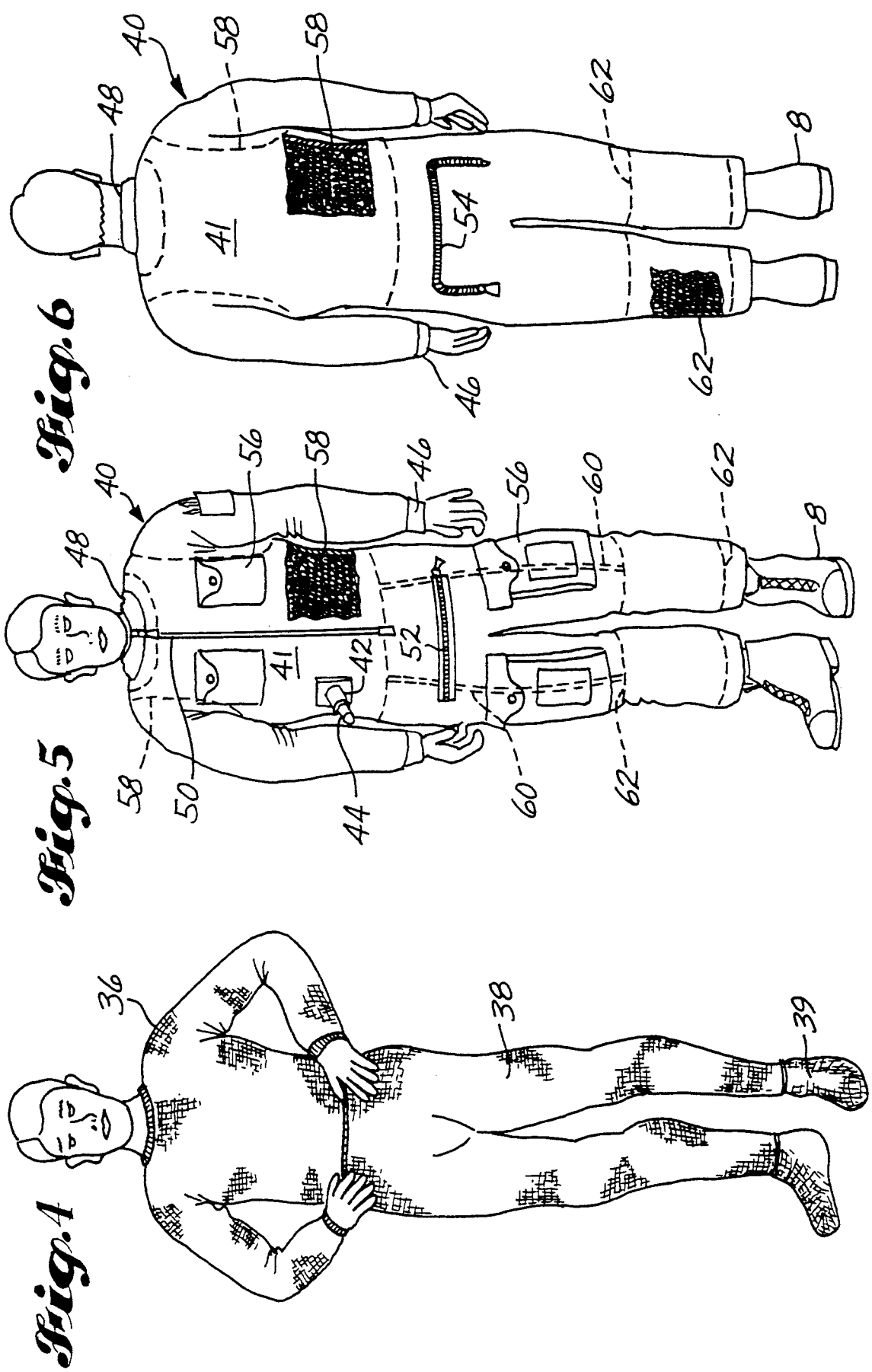

PILOT'S ENSEMBLE WITH INTEGRATED THREAT PROTECTION

GOVERNMENT RIGHTS

This invention was made with Government support under Contract No. F33657-86-C-2085 awarded by the United States Air Force. The Government has certain rights in this invention.

TECHNICAL FIELD

This invention relates to ensembles for clothing and protecting pilots and other crew members of aircraft and, more particularly, to such an ensemble with relatively few components designed to optimize the balance between the need to protect the pilot and the desirable goal of minimizing burdens on the pilot, and to permit the selective doffing of components when the threats they protect against are not present.

BACKGROUND INFORMATION

Modern high performance military aircraft subject crew members to a number of severe flight conditions. In addition, some types of missions have the potential to expose crew members to various kinds of threats from hostile forces. The flight conditions include conditions relating to the aircraft environment during normal operation of the aircraft, as well as conditions encountered in combat and emergency situations and during and following ejection. Normal operation may involve extremely high altitude and/or G forces, extreme temperatures, and high levels of noise and sun glare. Extraordinary conditions a crew member may face include fire in the aircraft, impact blows to the head region, wind blast during ejection, and cold water immersion following ejection or a crash. Possible hostile threats include chemical and biological (CB) weapons; directed energy weapons, such as lasers; and the effects of nuclear weapons. Such effects include prompt or immediate effects, e.g., nuclear flashes, and residual effects, e.g. nuclear dust.

Because of the large number and wide variety of severe conditions and threats that pilots and other crew members may be subjected to, there are numerous requirements relating to pilot ensembles used by crew members of current aircraft. In regard to future more sophisticated tactical aircraft, there will be even more requirements. The additional requirements will relate to factors such as the potential exposure of the crew members to new or more severe conditions and threats. In the future, provision of adequate protection for crew members is likely to be increasingly complicated by the increasing use of new technology, such as helmet mounted display (for displaying computer generated images to a pilot) and night vision goggle technology, and possibly additional technologies that have not yet entered an initial stage of development.

The current approach to pilot protection is piecemeal. In other words, in general a separate garment or component has been provided for each type of protection requirement. The numerous separate components have been developed with little, if any, regard for their integration into an overall system. The result is that current military inventory includes numerous separate components each of which may work well for its intended narrow protection purpose but is not designed to interface with other components in a way that optimizes the overall protection and comfort of the pilot. When a pilot is faced with a mission that may present multiple severe conditions and threats, he must wear multiple garments and may have to stack multiple components onto his helmet (if possible) in order to meet all the relevant protection requirements.

The negative impacts on the pilot of this piecemeal approach are numerous. The bulk and weight of the multiple components, in themselves, can be a serious burden on the pilot. In addition, the components can degrade the pilot's comfort, vision, mobility, and tactility (tactile sensitivity). Multiple garments can also place a severe thermal burden on the pilot, i.e. they can result in overheating of the pilot's body. With regard to protection against chemical and biological weapons, the current approach tends to overprotect the pilot, thereby increasing the burdens on the pilot. This situation is further aggravated by the fact that doffing of the chemical/biological protective equipment during flight to remove the encumbrance cannot be accomplished using known protective approaches. This is true even if the threat is no longer present, such as when the cockpit has been kept clean of liquid agents and vapor agents have been purged via the environmental control system.

A current pilot ensemble typically includes a flight suit and an anti-G suit worn over the flight suit. The flight suit is normally made from a flame resistant material, such as Nomex (trademark). It is currently anticipated that pilots of future high performance aircraft and future generations of current high performance aircraft will wear an upper pressure garment in addition to the flight suit and anti-G suit. In both current ensembles and currently anticipated future ensembles, the pilot wears a helmet with an oxygen mask and a visor. If laser protection is required for a mission, a laser visor is worn. If nuclear flash protection is required, nuclear flash goggles are worn separately.

The present approach to providing chemical/biological threat protection involves the addition of several components to the ensemble. These components include charcoal underwear that is worn under the flight suit. Hand protection is provided by a rubber glove and a cotton insert worn under the rubber glove, both of which are worn under the normal flight glove. Protection for the head and neck is provided by an impermeable butyl rubber hood to which a visor and oxygen mask are integrally attached. The impermeable hood assembly is worn under the pilot's helmet. This arrangement results in major problems relating to sweat buildup and thermal burdens on the pilot. It also has the significant disadvantage of not allowing the pilot to doff the C/B protection components in flight when there is no immediate threat of exposure. The lack of doff-ability of the hood is a major factor in the problems of sweat buildup and overheating. It also causes pilot discomfort in situations in which access to the face is needed, such as when the pilot has a runny nose or an eyelash in the eye or, worse, has to vomit.

In situations in which protection of the pilot against cold water immersion is required, the pilot typically wears an anti-exposure garment. In known ensemble approaches, the anti-exposure garment may be worn either under the flight suit or over the flight suit. Very few anti-exposure garments have ventilation capability. Therefore, anti-exposure garments typically impose a significant thermal burden on the pilot.

The integration of helmet mounted display and night vision goggle technology into pilot ensembles is in a developmental stage. To date, known proposals have not adequately addressed an acceptable method of integrating these technologies with chemical/biological, laser, and nuclear flash protection.

DISCLOSURE OF THE INVENTION

A subject of the present invention is an ensemble for use by an occupant of an aircraft. According to an aspect of the invention, the ensemble includes a garment configured to continuously cover the torso, arms, and legs of the occupant; a helmet; a hood; a breathing mask; and goggles. The garment has openings through which extremities and the head of the occupant extend. The garment also has a sealable ventilation port. The garment is impermeable to liquids and gases, and has seals around the openings, to protect the occupant's torso, arms, and legs from contact with gaseous and liquid agents. Upper and lower pairs of opposite mounting members are carried by front side portions of the helmet. The hood is configured to cover the head, neck, and shoulders of the occupant and to fit over neck and shoulder portions of the garment and under the helmet. The hood has an opening for the occupant's face, permeable head portions, and neck portions capable of absorbing chemical vapors. The mask is removably attachable to the lower pair of mounting members on the helmet. The goggles are removably attachable to, the upper pair of mounting members. The goggles have peripheral portions that seal the ocular region of the occupant's face. They also have an outer peripheral flap positioned to overlap the mask and the hood to cooperate with the mask and the hood to completely cover the occupant's face. The goggles and mask are removable, without doffing the helmet, while the occupant is wearing the helmet.

The ensemble preferably further comprises an overcape configured to fit over the helmet, the goggles, the mask, and upper portions of the garment. The overcape has transparent front portions to allow the occupant to see, and is impermeable to liquids. The overcape feature makes maximum protection of the pilot against liquid agents available in situations in which such protection is required. The overcape cooperates with the garment and suitable hand and foot protection to protect the entire body of the pilot from contact with liquid agents. When the threat of liquid agents is not present or has been removed, the overcape can be omitted or doffed to increase the pilot's comfort and mobility.

In the ensemble of the invention, the components may be provided with various preferred and/or optional features. Such features include a helmet passageway and a garment lining, both of which are described further below.

Another subject of the invention is headgear for use by an occupant of an aircraft. The headgear includes a helmet and a breathing mask, as described above, and a hood configured to cover the head, neck, and shoulders of the occupant and to fit under the helmet. The hood has an opening for the occupant's face, permeable head portions, and neck portions absorbent to chemical vapors. The headgear also includes goggles, as described above. A passageway in the helmet extends from an inlet end to the goggles when the goggles are attached to the upper pair of mounting members. The passageway routes breathing gas to a portion of the goggles inside the peripheral portions that seal the ocular region of the occupant's face.

The peripheral flap, of the goggles may take various forms. The flap may be impermeable to liquids and gases and be configured to form a seal against the mask and the hood. Alternatively, the flap may be permeable to liquids and gases and capable of absorbing chemical vapors.

Still another subject of the invention is a garment for use by an occupant of an aircraft. According to an aspect of the invention, the garment comprises an outer shell configured to continuously cover the torso, arms, and legs of the occupant. The shell has openings through which extremities and the head of the occupant extend, and a sealable ventilation port. The shell is impermeable to liquids and gases, and has seals around its openings, to protect the occupant's torso, arms, and legs from contact with gaseous and liquid agents. A lining is bonded to an inner surface of a torso portion of the shell. The lining is in communication with the ventilation port to receive air therefrom. The lining is sufficiently permeable to allow air from the port to flow through the lining along the shell's inner surface and out of the lining inwardly toward the occupant's torso, to regulate the occupant's body temperature.

The ventilation of the occupant's body is preferably enhanced by the routing of air flow to lower portions of the occupant's legs. This can be accomplished by providing a conduit that extends from the lining to lower leg portions of the garment. In the currently preferred embodiment, there are second and third linings, in addition to the first torso lining described above. The second and third linings are bonded to right and left lower leg inner surface portions, respectively, of the shell. These additional linings are separate and spaced from each other and from the first lining, and are sufficiently permeable to allow air flow therethrough along the inner surface portions of the shell to which they are bonded and inwardly toward the occupant's legs. The conduit extends between the first lining and each of the second and third linings to direct air flow between the first lining and the second and third linings. This arrangement provides efficient cooling or warming of, the aircraft occupant's body while minimizing the impact on the occupant of the temperature regulation system.

As described above, the garment of the invention has openings through which extremities of the occupant extend. It is anticipated that, in most circumstances, the hands of the occupant will extend through openings in the outer shell of the garment to allow the use of separately removable gloves that can be doffed when not needed to maximize the dexterity and tactility of the occupant. The feet of the occupant may either extend through openings in the outer shell or be covered by socks that are integral with the shell.

The invention provides a minimum number of optimized components to greatly mitigate the problem of burdens on the pilot without sacrificing the effectiveness of the protection afforded the pilot. A major advantage of the invention is that it makes effective protection against chemical and biological agents available with substantially no detrimental effect on the pilot under normal flight conditions and minimized impacts in situations in which a CB threat is actually present and the related threat components are in use. The helmet-mounted goggles can be doffed in flight to increase the pilot's comfort and vision. The breathing mask may also be doffed during flight, when not needed, for greater in-flight comfort. Although the hood cannot be removed without removing the helmet, since it fits under the helmet, its presence during flight has minimal impact on comfort because of its permeable head portions. The garment of the invention is intended to be worn during flight instead of a conventional flight suit. The impermeability of the garment protects the pilot against cold water immersion as well as chemical and biological threats should the need arise. The preferred feature of a bonded lining allows the garment to be worn under normal flight conditions as comfortably as a conventional flight suit. The lining provides an effective means of preventing thermal burdens on the pilot's body and of regulating the pilot's body temperature with only minimal, if any, impact on the pilot's mobility and the bulk and weight of his ensemble.

In addition to minimizing burdens on the pilot, the design of the CB protective components of the invention provides better overall protection for the pilot. The components, including the overcape of the preferred embodiment, can be decontaminated while they are being worn. This greatly simplifies the decontamination procedure and helps eliminate any danger of exposure of the pilot to CB agents during doffing of ensemble components. The capacity of the mask to be detached from the helmet also protects the wearer from suffocation (drowning) in the event of ejection over Water. The mask can be easily removed following ejection.

The apparatus of the invention maximizes the comfort, vision, mobility, and tactility of the wearer. In addition, the apparatus of the invention is highly versatile. It can be worn without a pressure garment or, as needed, with various existing types of pressure garments. It also can readily accommodate the addition of new components. This latter capability will facilitate the integration into the ensemble of the invention of new technologies, such as the helmet mounted display and night vision goggle technology mentioned above. Moreover the minimizing of the number of components and the elimination of overprotection achieved by the invention help make the overall protection package more cost effective.

These and other advantages and features will become apparent from the detailed description of the best mode for carrying out the invention that follows.

BRIEF DESCRIPTION OF THE DRAWINGS

In the drawings, like element designations refer to like parts throughout, and:

FIG. 1 is a pictorial view of a pilot wearing a conventional flight suit.

FIG. 2 is a pictorial view of a pilot wearing the flight suit shown in FIG. 1 and upper and lower pressure garments over the flight suit.

FIG. 3 is a pictorial view of a type of upper body air garment worn under conventional flight suits.

FIG. 4 is a pictorial, view of a pilot wearing a type of long underwear that is compatible with the apparatus of the invention.

FIG. 5 is a pictorial view of a pilot wearing the preferred embodiment of the garment of the invention, with portions of the garment outer shell cut away to reveal the inner lining.

FIG. 6 is like FIG. 5 except that it is looking toward the back of the pilot.

BEST MODE FOR CARRYING OUT THE INVENTION

Figure 8:
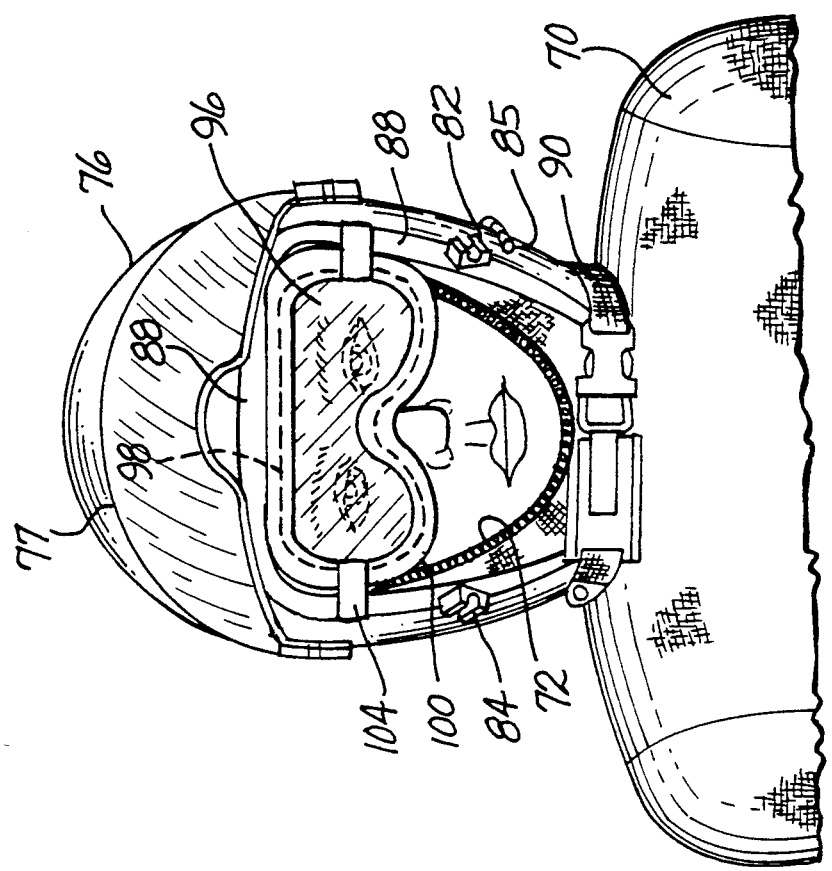
FIG. 8 is like FIG. 7 except that it shows the pilot also wearing a helmet and goggles.
Figure 7:
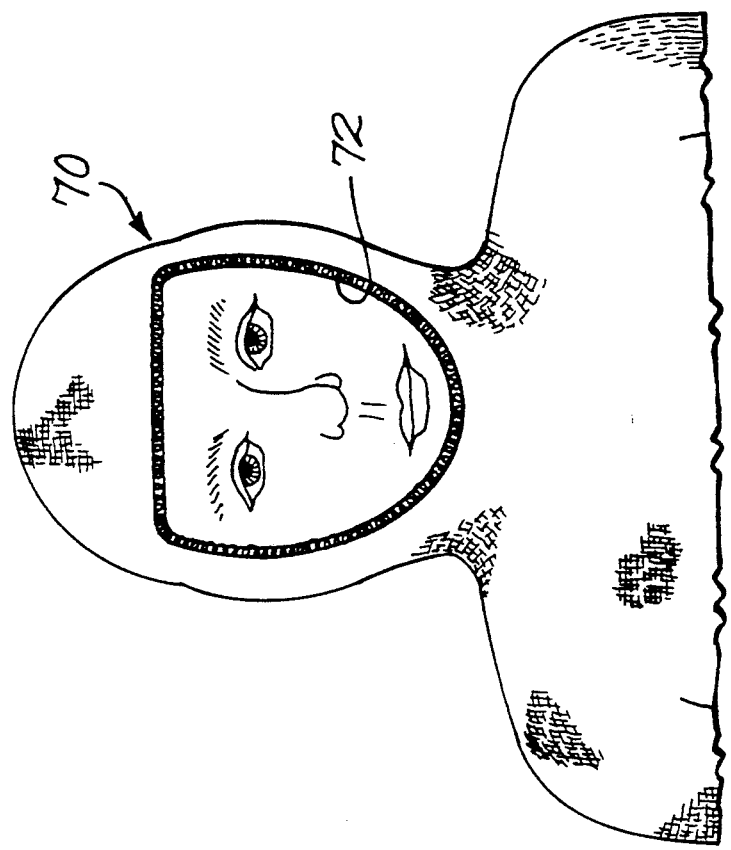
FIG. 7 is an elevational view of the head and shoulder region of a pilot wearing the hood of the invention.

The drawings show apparatus that is constructed according to the invention and that constitutes the best mode of the invention currently known to the applicants. The apparatus of the invention is intended primarily for use by pilots of high performance military aircraft but may be used by pilots of other types of aircraft and by other occupants of various types of aircraft. The details of the elements of the invention may, of course, be varied without departing from the spirit and scope of the invention. For example, the drawings show a generalized helmet structure of a known type into which basic elements of the invention have been incorporated. In particular applications of the invention, it is likely that the helmet design will be modified in order to accommodate helmet mounted systems, such as helmet mounted display and/or night vision goggle systems. The details of the helmet design in such cases would be dependent upon the type of helmet mounted system to be incorporated.

To assist in putting the invention into perspective, FIGS. 1-3 show pilot ensemble components that are currently known to the industry and/or the military. FIG. 1 is a pictorial view of a pilot wearing a conventional type of flight suit 2 and boots 8. The suit 2 includes a zipper 6 for donning and doffing and has been modified to include an air hose pass-through opening 4. FIG. 2 shows the pilot in FIG. 1 wearing an upper pressure garment 12 and a lower pressure garment 18 over the flight suit 2. The upper garment 12 has an air hose pass-through opening 14 and an entry zipper 16. The lower garment 18 also has entry zippers (not shown) located, for example, along the inseams of the garment 18. The lower garment 18 is of a type that is currently part of standard military inventory. The upper garment 12 is relatively new. The upper garment 12 covers the torso of the wearer above the waist, and the lower garment 18 covers the torso below the waist and the legs, to provide the wearer with protection against high G forces. The pressure garments 12, 18 have inflatable bladders and operate in a known manner in order to provide this type of protection.

FIG. 3 shows a relatively new type of air garment 22. This garment 22 is designed to be worn under a flight suit, such as the suit 2 shown in FIGS. 1 and 2, to provide a means for regulating the body temperature of the wearer. The vest-like air garment 22 has elastic shoulder straps 24 with vertical adjustment fittings 26 and an elastic cummerbund 28 that is preferably provided with girth adjustment fittings (not shown). The inside of the body of the garment 22 is lined with a mesh-like material 32 that resembles a plastic scouring pad and is permeable to air. The garment 22 is provided with an air inlet fitting 30 that is connectable to an air hose to deliver air to the mesh material 32. When a pilot is outfitted in the flight suit 2, pressure garments 12, 18, and air garment 22 shown in FIGS. 1-3, the fitting 30 extends through the openings 4, 14 in the flight suit 2 and upper pressure garment 12. The fitting 30 is connected to an environmental control system hose. Air flows in through the fitting 30 and through the mesh material 32 around the torso of the pilot to regulate the pilot's body temperature.

The ensemble illustrated in FIGS. 1-3 is suitable for use in most normal operations in which hostile threats, such as chemical and biological weapons, are not likely to be encountered. However, it does not provide any protection against chemical/biological threats and is, therefore, not suitable for other types of missions. For normal missions, some of the elements of the ensemble shown in FIGS. 1-3 may be omitted. The upper pressure garment 12 and/or the lower pressure garment 18 may be selectively worn or not worn as required by the mission. The air garment 22 would normally be worn under the flight suit 2 only for warm and/or cold weather operations. During these types of operations, conditioned air from the environmental control system of the aircraft would be provided to the pilot's body to the mesh lining 32 of the air garment 22 for either heating or cooling the pilot's body. For missions that require threat protection, additional components must be added to the ensemble shown in FIGS. 1-3 in order to provide chemical/biological protection, protection for cold water immersion situations, and protection against additional kinds of threats. Regardless of the nature of the mission, the pilot also typically wears or is provided with conventional components, such as a helmet, an oxygen mask and a visor. The additional components of known types of pilot ensembles are discussed above under the heading "Background Information".

The major goal of the invention is to provide a pilot's ensemble that performs all of the functions of the ensemble shown in FIGS. 1-3, effectively provides a full range of threat protection, and, at the same time, reduces the burdens on the pilot, in comparison to the use of conventional ensembles. This goal is accomplished by modifying conventional components and integrating the required threat protection in an optimum manner. The preferred embodiment of the invention is illustrated in FIGS. 4-17.

Referring to FIGS. 5 and 6, the ensemble of the invention includes a body garment 40 that replaces the conventional flight suit 2. The garment 40 performs the major functions of the flight suit 2, i.e. flame protection and clothing the pilot. It also provides protection against chemical/biological agents and cold water immersion. FIG. 4 shows a type of long underwear 36, 38 that is preferably worn under the garment 40. The underwear 36, 38 is intended to serve the usual purpose of underwear and also to protect the skin of the pilot against contact with other components of the ensemble which could be irritating to the skin. The underwear 36, 38 has an upper portion 36 and a separate lower portion 38, both of which are preferably made from a very lightweight soft cotton. The upper and/or lower pressure garments 12, 18 shown in FIG. 2, or other suitable pressure garments, may be worn over the garment 40 of the invention, as needed.

Referring again to FIGS. 5 and 6, the garment 40 includes an outer shell 41 which forms the main body of the garment 40. The shell 41 is configured to continuously cover the torso, arms, and legs of the wearer. The shell 41 is made from an abrasion resistant material that is impermeable to liquids and gases and has a sealable ventilation port 42 and a sealable entry zipper 50. The port 42 is provided with a fitting 44, which is preferably self-sealing. The shell 41 also has additional elements, such as pockets 56 and front and rear sealable relief zipper's 52, 54 for eliminating body wastes without doffing the garment 40. The entry and relief zippers 50, 52, 54 may be varied in location and orientation. Optimum zipper configurations have not yet been determined.

The outer shell 41 of the garment 40 has openings through which extremities and the head of the wearer extend. In the currently preferred embodiment, the head and hands of the wearer extend through neck and wrist openings. Wrist seals 46 and a neck seal 48 are provided to prevent passage of liquid and gaseous agents through the openings and, thereby, ensure the effectiveness of the outer shell 41 in protecting the body of the wearer against such agents. The neck seal 48 is preferably of a type used on dry suits and known types of cold water immersion protection garments. The wrist seals 46 have a similar construction. The seals 46, 48 are preferably made from a type of rubber.

Figure 13:
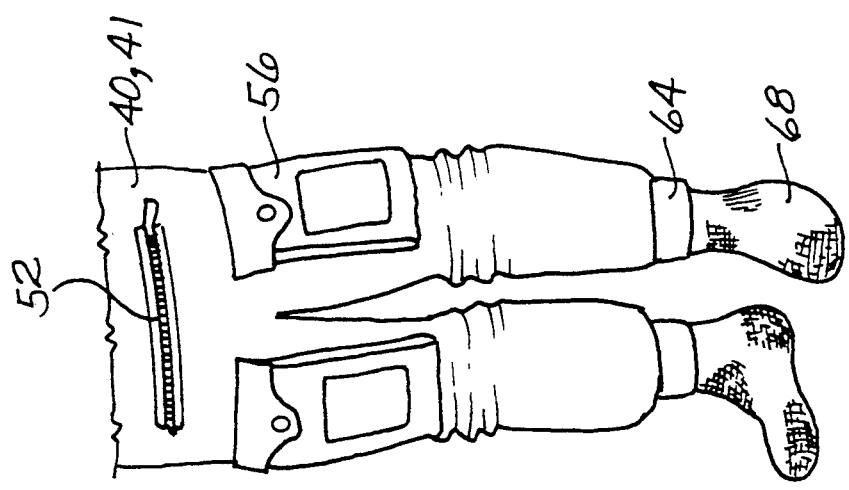
FIG. 13 is like FIG. 12 except that it illustrates a modification of the preferred embodiment.
Figure 12:
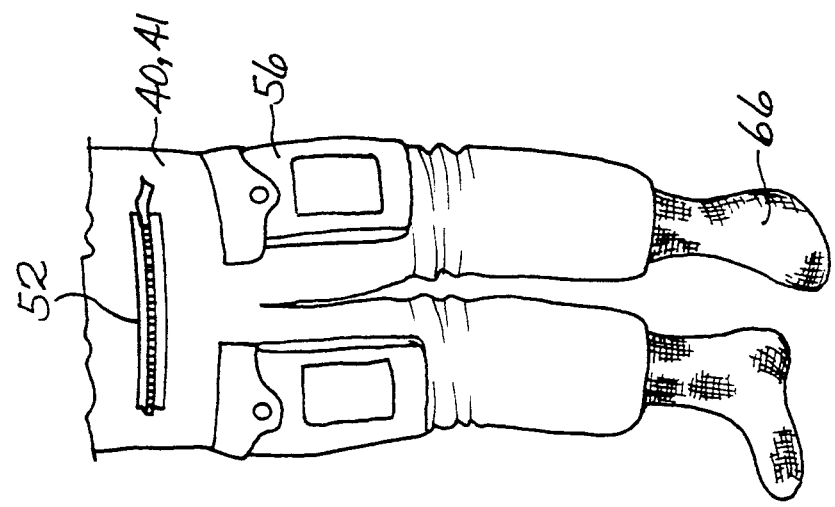
FIG. 12 is a pictorial view of the lower portion of the body of a pilot wearing the preferred embodiment of the garment without boots.

The garment 40 is preferably provided with integral socks 66, illustrated in FIG. 12. These socks 66 are preferably impermeable to gases and liquids, like the main portion of the garment shell 41 to which they are integrally attached. Impermeable socks 66 protect the wearer against cold water and liquid agents even if the flight boots 8 become saturated with liquid. Separate permeable socks 39 (FIG. 4) may be worn under the garment's socks 66 to maintain the comfort of the wearer's feet. Although the integral impermeable socks 66 are preferred, the garment 40 could also be provided with ankle seals 64, as shown in FIG. 13. In such case, separate socks 68 would be worn with the garment 40. The socks 68 are preferably impermeable and may be worn over permeable socks.

The garment 40 is provided with a torso lining 58, 58' integrally bonded to the inner surface of the upper torso portion of the shell 41. The lining 58, 58' has an overall vest-like configuration extending all the way around the torso and over the shoulders of the shell 41. A front lower torso portion of the lining 58, 58' is in communication with the ventilation port 42 to receive air therefrom. The air is supplied by an air hose connected to the aircraft's environmental control, system. The lining 58, 58' is sufficiently permeable to allow air from the port 42 to flow through the lining 58, 58' along the inner surface of the shell 41 and out of the lining 58, 58' inwardly toward the wearer's torso, to regulate the wearer's body temperature. As illustrated in FIG. 6, the lining 58 may be made from the type of material 32 illustrated in FIG. 3 and described above. The integral bonding of the lining 58, 58' to the garment shell 41 eliminates the need for a separate air garment and minimizes the bulk and weight added to the ensemble by the inclusion of the ventilation feature.

Figure 17:
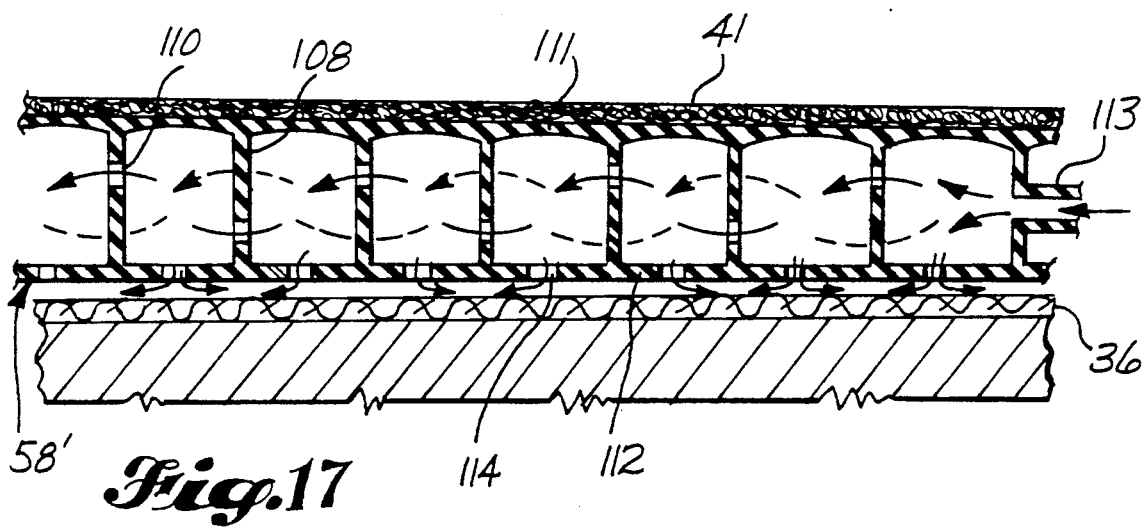
FIG. 17 is a cross-sectional view of another embodiment of the garment torso lining.

An alternative embodiment of the lining 58' is illustrated in FIG. 17. Like the lining 58 shown in FIG. 6, the lining 58' is bonded to the inner surface of the torso portion of the shell 41. The lining 5B' has an outer wall 111 that is bonded to the shell 41 and a spaced parallel inner wall 112. A plurality of ribs 108 extend between the walls 111, 112 to maintain them in a spaced relationship. Air is supplied to the space between the walls 111, 112 through a port 113. The ribs 108 have openings 110 extending therethrough to allow air to flow through the ribs 108 between the walls 111, 112, as illustrated by the arrows in FIG. 17. The inner wall 112 has openings 114 to allow air to flow out of the lining 58' toward the wearer's torso. Air flowing out of the lining 58' through the openings 114 flows along and through the permeable undergarment 36 to cool or warm the wearer's skin.

Providing cooling or warming air to the torso of the wearer accomplishes most of the required body temperature regulation. However, the comfort of the pilot can be enhanced and the temperature regulation improved by supplementing the torso lining 58, 58' with means for delivering air to the legs and/or arms of the wearer. Air can be delivered to a limb by a conduit from the torso lining 58, 58' to the limb. The far end of the conduit may simply have holes therein to deliver air to the limb. Alternatively, the limb area of the garment may be provided with a lining through which the air is directed.

In the illustrated embodiment, separate linings 62 are located in leg portions of the garment 40. As shown in FIGS. 5 and 6, the two leg linings 62 are integrally bonded to the right and left lower leg inner surface portions, respectively, of the shell 41. Each leg lining 62 extends all the way around the leg portion to which it is bonded. The leg linings 62 are preferably made from the same type of material as the torso lining 58 and permit air flow around the respective leg portions of the shell 41 along the inner surface of the shell 41. The three linings 58, 62 are spaced from each other but are interconnected so that they may be supplied by a single ventilation port 42. A conduit between the leg linings 62 and the torso lining 58 is provided to direct air flow from the torso lining 58 to the leg linings 62. As shown, the conduit has two separate branches formed by right and left tubes 60 extending downwardly from the torso lining 58 to the respective leg linings 62. The tubes 60 may be made from various materials, such as plastic or rubber.

Air flow through the combination of the three separate linings 58, 62 effectively cools or warms the entire body of the wearer. The cooling or warming of the surface skin temperature and blood flow in the body regions immediately adjacent to the linings 58, 62 is enhanced by the seepage of air from the linings 58, 62 to other portions of the body. This seepage also helps to maintain the effectiveness of the sealing of the body against liquid and gaseous agents by creating a positive pressure inside the garment 40 which results in leakage through the seals 46, 48 in an outward direction and, thereby, prevents leakage in an inward direction.

The ensemble of the invention also includes headgear that provides a full range of protection for the pilot. The preferred embodiment of the headgear is illustrated in FIGS. 7-11 and 14-16. The headgear includes a helmet 76, shown in FIGS. 8-11, 14, and 15, which performs the usual function of protecting the pilot's head against impact blows and also provides a means for mounting other protective elements on the pilot's head. The headgear also includes a hood 70, best seen in FIG. 7. The hood 70, is configured to cover the head, neck, and shoulders of the pilot and has an opening 72 for the pilot's face. When the ensemble is donned by a pilot, the body garment 40 is donned first, and then the hood 70 is donned. The hood 70 fits over neck and shoulder portions of the garment 40 and under the helmet 76, as shown in FIGS. 8-10, 14, and 15. At least the portion of the hood 70 under the helmet 76, and preferably the entire hood 70, is permeable for the pilot's comfort. The permeability avoids the problems of sweat buildup and thermal burdens discussed above in connection with the current butyl rubber hood. The portion of the hood 70 not covered by the helmet 76 is capable of absorbing chemical vapors to protect the pilot's skin in the neck area and around the face opening 72 from contact with chemical vapors. The absorbing capability can be provided, for example, by impregnating the thin lightweight material of the hood 70 with charcoal. The portion of the hood 70 covered by the helmet serves the function of a skull cap to keep the helmet liner clean. It also allows the pilot's head to breathe and wicks sweat away from the pilot's head for evaporation.

Figure 9:
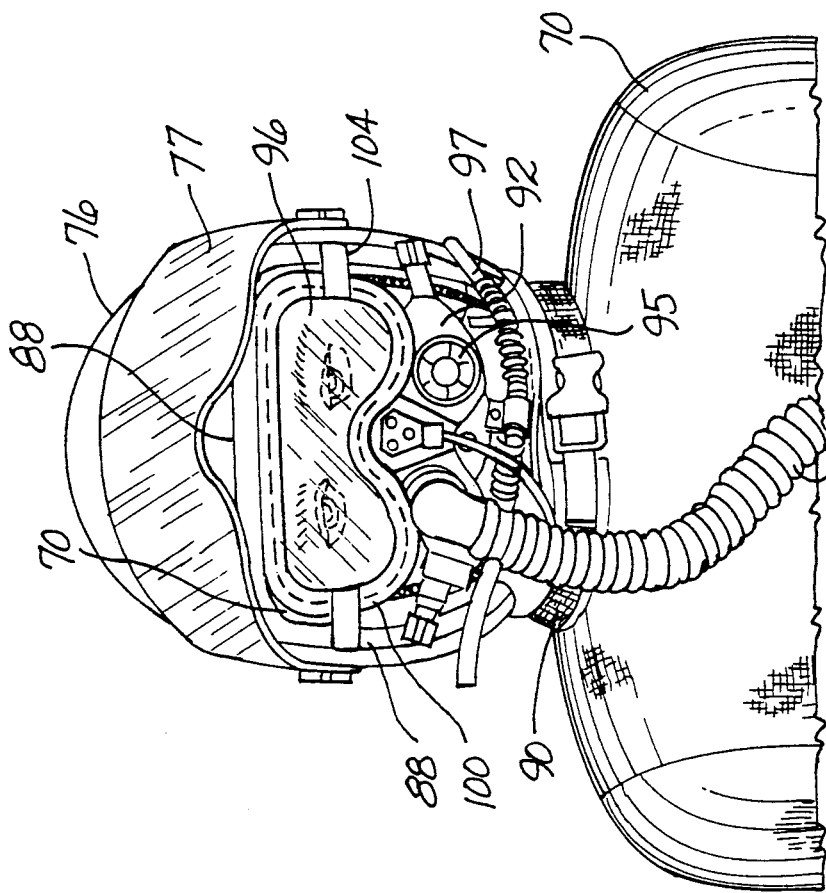
FIG. 9 is like FIG. 8 except that it shows the pilot also wearing a breathing mask.
Figure 14:
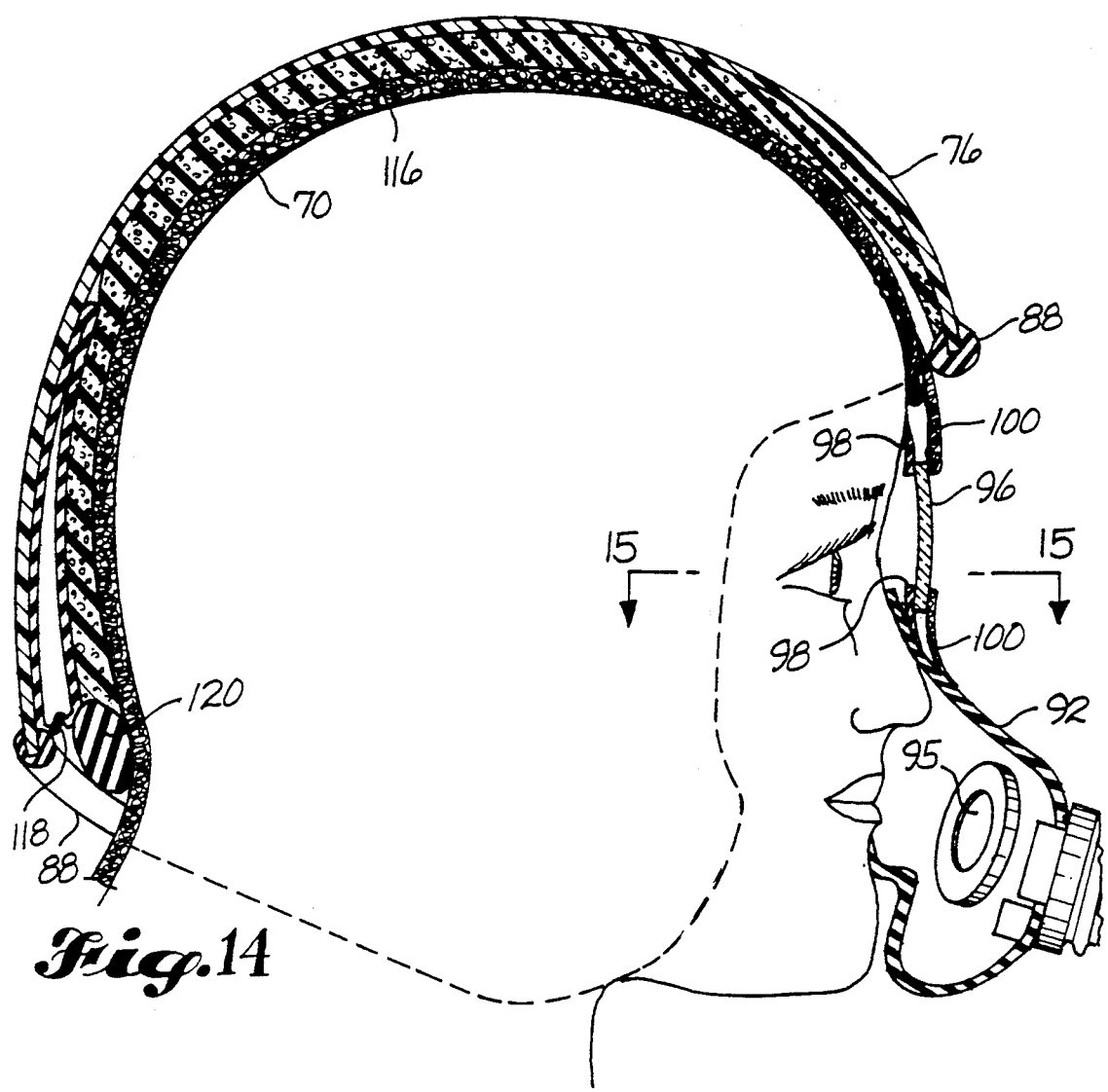
FIG. 14 is a side elevational view of the head of a pilot wearing the apparatus shown in FIG. 9, with the apparatus shown in section.
Figure 15:
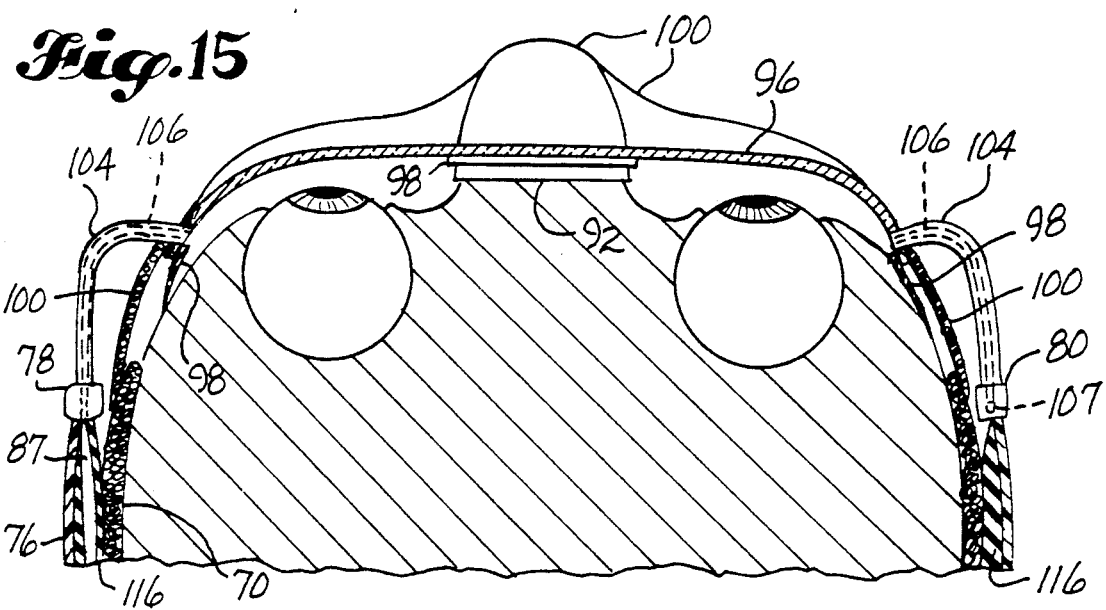
FIG. 15 is a sectional view taken along the line 15—15 in FIG. 14.

As noted above, the helmet 76 protects the pilot's head against impact blows. The illustrated helmet 76 has a number of conventional features, including a chin strap 90, an energy absorbing lining 116, an edge roll 88, a rear cushion 120, and an inflatable bladder 118 (FIG. 14). Inflation of the bladder 118 achieves a snug fit of the breathing mask 92 (described below) on the pilot's head and thereby provides mask sealing during pressure breathing. Additional protective elements for the pilot's eyes and face are mounted on the helmet 76. These elements include a visor 77 of a known type. The helmet 76 is provided with mounting members for mounting protective goggles 96 and a breathing mask 92. The mounting members are arranged in two pairs of members with the two members in each pair being carried by opposite front side edge portions of the helmet 76. The goggles 96 are mounted on the upper pair of mounting members 78, 80, and the mask is mounted on the lower pair 82, 84. The goggles 96 engage the upper mounting members 78, 80 by means of laterally and rearwardly projecting connectors 104 (FIGS. 8-10 and 15). The goggles 96 and mask 92 are each removably attachable to the corresponding pair of mounting members to permit the pilot to selectively don and doff these two elements while wearing the helmet 76, without removing the helmet 76. When the mask 92 is donned, the hood 70 is pulled down and then released so that it extends over the chin and cheek portions of the mask 92, as shown in FIG. 9.

The goggles 96 protect the ocular region of the pilot's face and are shaped similarly to ski goggles. The goggles 96 have a peripheral seal 98 that seals against the pilot's face and the nose portion of the mask 92 to seal the ocular region of the pilot's face and thereby protect it against liquid and gaseous agents. The seal 98 may be made, for example, from a rubber material resistant to chemical agents, including decontaminants. The goggles 96 also include an outer peripheral flap 100 that is positioned to overlap the hood 70 and the upper portions of the mask 92 to cooperate with the hood 70 and the mask 92 to completely cover the pilot's face. As shown in FIG. 14, the flap 100 may be tucked under the edge roll 88 of the helmet 76. The flap 100 may be made from an impermeable material, such as rubber, to seal against the mask 92 and the hood 70. Alternatively, the flap 100 may be made from a vapor absorbent material similar to, but heavier than, the vapor absorbent neck portion of the hood 70, or a combination of an impermeable material and an absorbent material. The configuration of the goggles 96 and the manner in which they cooperate with the other face protection elements minimize obstruction of the pilot's vision and allow integration of the chemical/biological protection beneath other helmet mounted systems which may be added for a particular type of mission.

The mask 92 may be any of a variety of known types with modifications to meet the requirements of the invention. For example, the mask is configured to detachably engage the lower mounting members 82, 84. Preferably, the engagement of the members 82, 84 will automatically detach when the pilot lands in water following ejection. The technology for automatic disengagement has been developed separately and is not a part of the present invention. The dimensions of the mask 92 will also generally require modification so that the goggle flap 100 will overlap the upper portion of the mask 92. The mask 92 has a fitting to which an air hose 94 of a known type is attached to supply the pilot with filtered air from the aircraft environmental control system. Exhaled air is exhausted through an exhalation valve 95.

Figure 11:
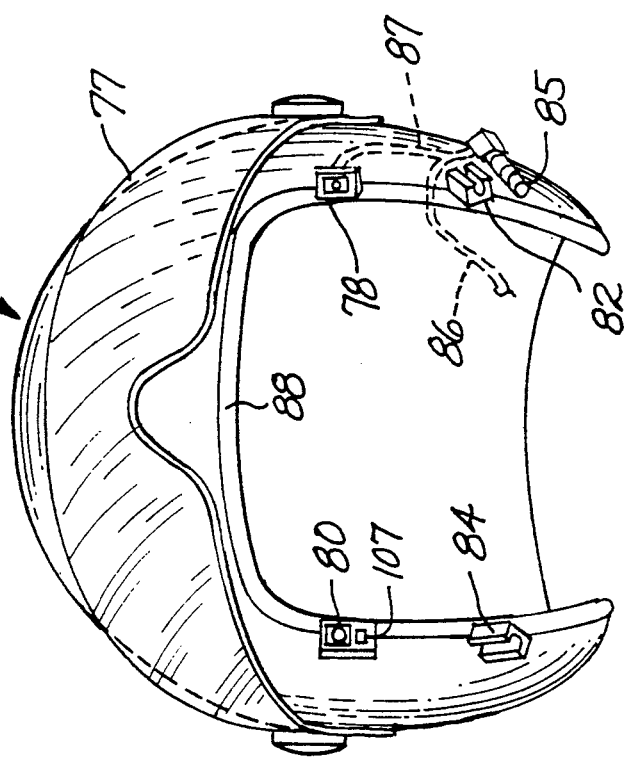
FIG. 11 is a front view of the helmet shown in FIGS. 8-10.
Figure 16:
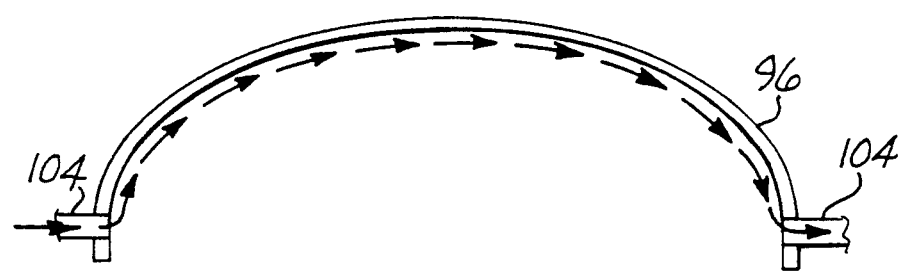
FIG. 16 is a schematic plan view of the goggles shown in FIGS. 14 and 15, illustrating the defogging air flow.

Referring to FIG. 11, a passageway is formed in the helmet 76 to route filtered air from the air hose 94 to the bladder 118 and the ocular cavity of the pilot inside the peripheral seal 98 on the goggles 96. The passageway inlet may be formed through the mounting member 82. However, in the illustrated preferred embodiment, it is formed by a hose fitting 85 on the side of the helmet 76 behind the mounting member 82. A supply hose 97 extends from the main air hose 94 to the fitting 85. The passageway extends from the fitting 85 through the helmet lining 116 and divides into two separate passageways 86, 87. The first passageway 86 extends rearwardly to the bladder 118. The second passageway 87 extends to the upper right mounting member 78. Air from the passageway 87 flows through the member 78 and through a passageway 106 in the corresponding goggle connector 104 which opens onto a surface of the connector 104 inside the pilot's ocular cavity and the goggle seal 98. The supplying of filtered air to the goggles 96 prevents the goggles 96 from fogging to maintain the pilot's ability to see, In addition, it provides a pressurization of the ocular cavity above ambient pressure to prevent leakage of gases into the ocular cavity past the peripheral seal 98. A one-way relief valve 107 (FIGS. 11 and 15) in the left mounting member 80 allows air to escape to atmosphere to avoid overpressurization and maintain the integrity of the seal 98. The flow pattern through the goggles 96 is illustrated in FIG. 16. The mask 92 similarly prevents inboard leakage to prevent exposure of the lower portion of the pilot's face.

Figure 10:
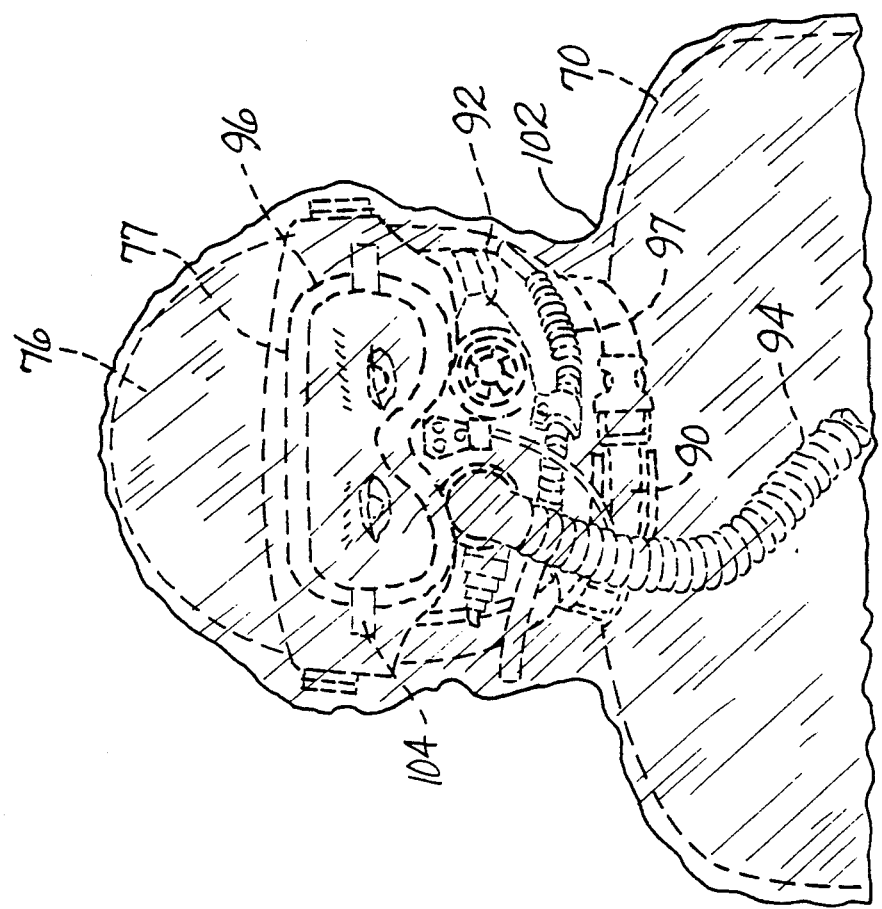
FIG. 10 is like FIG. 9 except that it shows an overcape being worn over the other components of the pilot's ensemble.

The chemical/biological protective components of the ensemble include the additional elements of the overcape 102 shown in FIG. 10, overgloves, and overboots. The overcape 102 is configured to fit over the helmet 76, the goggles 96, the mask 92, and at least the upper portions of the body garment 40. Preferably, the overcape 102 extends most of the way down to the knees of the pilot. The overboots (not shown) are simply loose plastic boots that cover the flight boots 8. Both the overcape 102 and the overboots are currently in the military inventory. The overgloves (not shown) are designed to fit over the modified flight gloves of the invention and are essentially like the type of thin plastic gloves that can be purchased in any of a variety of retail stores. Once the overcape 102 is donned, it forms a seal to prevent liquid agents from contacting the upper body portions of the pilot. The purpose of the overcape 102, overboots, and overgloves is basically to protect the pilot from liquid agents when he is on the ground following exiting from the aircraft or prior to boarding the aircraft. These three elements are doffed during cockpit entry.

In accordance with the invention, basic chemical/biological hand protection is preferably provided by gloves that are similar to standard Nomex (trademark) flight gloves but are constructed of a Nomex material that is chemical vapor absorptive. This can be accomplished, for example, by impregnating the Nomex material with charcoal. The overgloves supplement the protection afforded by the modified flight gloves, as described above.

The lenses of the goggles 96 will normally be ordinary lenses, which may be tinted to reduce sun glare. In some situations, additional eye protection may be required. If protection against lasers is required for a particular mission, the normal goggle lens will be replaced with a laser protective coated lens. The goggles 96 are preferably provided with a holding frame to insert additional lenses under either the normal lenses or the laser protective lenses. Prescription lenses individualized to a particular pilot could be inserted into the goggle holding frame. The frame could also serve as a receptacle for lenses that protect against nuclear flash blindness.

The invention provides an overall combination of components that optimally integrate threat protection into a pilot's ensemble. The invention minimizes ensemble bulk and weight and optimizes the design of individual components to minimize impacts to and burdens on the pilot. With regard to the threat protection components, the invention has the important advantageous capabilities of selective inflight don-ability and doff-ability and ventilation to maintain the pilot's comfort and effectiveness. It also gives the pilot nose and eye access and permits the pilot to perform bodily functions, such as food and liquid intake, valsalva, and body waste removal. The ensemble of the invention is compatible with and has minimal impacts on other life support equipment on the aircraft The minimized bulk and weight of the ensemble also helps to maintain compatibility with other equipment in the cockpit, including the ejection seat, and other garmentry, such as cold weather gear. Moreover, the invention provides highly effective protection against the effects of cold water immersion, chemical/biological threats, and other threats, while maintaining the flexibility to omit specific threat protection components if a particular mission does not require them.

Although the preferred embodiment of the invention has been illustrated and described herein, it is intended to be understood by those skilled in the art that various modifications and omissions in form and detail may be made without departing from the spirit and scope of the invention as defined by the following claims.

What is claimed is:

1. An ensemble for use by an occupant of an aircraft, comprising:

a garment configured to continuously cover the torso, arms, and legs of the occupant; said garment having openings through which extremities and the head of the occupant extend, and a sealable ventilation port connectable to an external hose; and said garment being impermeable to liquids and gases, and having seals around said openings, to protect the occupant's torso, arms, and legs from contact with gaseous and liquid agents;

a helmet including a lower pair of opposite mounting members, and an upper pair of opposite mounting members; said pairs of mounting members being carried by front side portions of said helmet;

a hood configured to cover the head, neck, and shoulders of the occupant and to fit over neck and shoulder portions of said garment and under said helmet; said hood having an opening for the occupant's face, permeable head portions, and neck portions capable of absorbing chemical vapors;

a breathing mask removably attachable to said lower pair of mounting members, and having a fitting attachable to an external air hose; and goggles removably attachable to said upper pair of mounting members; said goggles having peripheral portions that seal the ocular region of the occupant's face, and an outer peripheral flap positioned to overlap said mask and said hood to cooperate with said mask and said hood to completely cover the occupant's face; and said goggles and said mask being removable, without doffing said helmet, while the occupant is wearing said helmet.

2. The ensemble of claim 1, comprising a passageway in said helmet; said passageway having an inlet end and extending from said inlet end to said goggles, when said goggles are attached to said upper pair of mounting members, to route breathing gas to a portion of said goggles inside said peripheral portions.

3. The ensemble of claim 2, in which said garment has an inner surface and includes a lining bonded to a torso portion of said inner surface; said lining being in communication with said port to receive air therefrom, and being sufficiently permeable to allow air from said port to flow through said lining along said inner surface and out of said lining inwardly toward the occupant's torso, to regulate the occupant's body temperature.

4. The ensemble of claim 3, in which said lining comprises a first lining; and which further comprises a second lining and a third lining bonded to right and left lower leg portions, respectively, of said inner surface; said second and third linings being separate and spaced from each other and from said first lining, and being sufficiently permeable to allow air flow therethrough along said surface and inwardly toward the occupant's legs; and a conduit extending between said first lining and each of said second and third linings to direct air flow between said first lining and said second and third linings.

5. The ensemble of claim 1, in which said garment has an inner surface and includes a lining bonded to a torso portion of said inner surface; said lining being in communication with said port to receive air therefrom, and being sufficiently permeable to allow air from said port to flow through said lining along said inner surface, to regulate the occupant's body temperature.

6. The ensemble of claim 5, in which said lining comprises a first lining; and which further comprises a second lining and a third lining bonded to right and left lower leg portions, respectively, of said inner surface; said second and third linings being separate and spaced from each other and from said first lining, and being sufficiently permeable to allow air flow therethrough along said surface; and a conduit extending between said first lining and each of said second and third linings to direct air flow between said first lining and said second and third linings.

7. The ensemble of claim 1, further comprising an overcape configured to fit over said helmet, said goggles, said mask, and upper portions of said garment; said overcape having transparent front portions to allow the occupant to see, and being impermeable to liquids.

8. Headgear for use by an occupant of an aircraft, comprising:

a helmet including a lower pair of opposite mounting members, and an upper pair of opposite mounting members; said pairs of mounting members being carried by front side portions of said helmet;

a hood configured to cover the head, neck, and shoulders of the occupant and to fit under said helmet; said hood having an opening for the occupant's face, permeable head portions, and neck portions capable of absorbing chemical vapors;

a breathing mask removably attachable to said lower pair of mounting members;

goggles removably attachable to said upper pair of mounting members; said goggles having peripheral portions that seal the ocular region of the occupant's face, and an outer peripheral flap positioned to overlap said mask and said hood to cooperate with said mask and said hood to completely cover the occupant's face; and said goggles and said mask being removable, without doffing said helmet, while the occupant is wearing said helmet; and a passageway in said helmet; said passageway having an inlet end and extending from said inlet end to said goggles, when said goggles are attached to said upper pair of mounting members, to route breathing gas to a portion of said goggles inside said peripheral portions.

9. The headgear of claim 8, in which said peripheral flap is impermeable to liquids and gases and forms a seal against said mask and said hood.

10. Headgear for use by an occupant of an aircraft, comprising:

a helmet including a lower pair of opposite mounting members, and an upper pair of opposite mounting members; said pairs of mounting members being carried by front side portions of said helmet;

a hood configured to cover the head, neck, and shoulders of the occupant and to fit under said helmet; said hood having an opening for the occupant's face, permeable head portions, and neck portions capable of absorbing chemical vapors;

a breathing mask removable attachable to said lower pair of mounting members;

goggles removably attachable to said upper pair of mounting members; said goggles having peripheral portions that seal the ocular region of the occupant's face, and an outer peripheral flap positioned to overlap said mask and said hood to cooperate with said mask and said hood to completely cover the occupant's face; said peripheral flap being permeable to liquids and gases and being capable of absorbing chemical vapors; and said goggles and said mask being removable, without doffing said helmet, while the occupant is wearing said helmet; and a passageway in said helmet; said passageway having an inlet end and extending from said inlet end to said goggles, when said goggles are attached to said upper pair of mounting members, to route breathing gas to a portion of said goggles inside said peripheral portions.

11. A garment for use by an occupant of an aircraft, comprising:

an outer shell configured to continuously cover the torso, arms, and legs of the occupant; said shell having openings through which extremities and the head of the occupant extend, and a sealable ventilation port connectable to an external hose; and said shell being impermeable to liquids and gases, and having seals around said openings, to protect the occupant's torso, arms, and legs from contact with gaseous and liquid agents; and a lining bonded to an inner surface of a torso portion of said shell; said lining being in communication with said port to receive air therefrom, and being sufficiently permeable to allow air from said port to flow through said lining along said inner surface and out of said lining inwardly toward the occupant's torso, to regulate the occupant's body temperature.

12. The garment of claim 11, in which said lining comprises a first lining; and which further comprises a second lining and a third lining bonded to right and left lower leg inner surface portions, respectively, of said shell; said second and third linings being separate and spaced from each other and from said first lining, and being sufficiently permeable to allow air flow therethrough along said inner surface portions and inwardly toward the occupant's legs; and a conduit extending between said first lining and each of said second and third linings to direct air flow between said first lining and said second and third linings.

13. The garment of claim 11, further comprising a conduit extending from said lining to lower leg portions of said garment, to direct air flow from said lining to the occupant's legs.

14. The garment of claim 1, in which the hands and feet of the occupant extend through said openings, and said seals seal around the neck, wrists, and ankles of the occupant.

15. The garment of claim 11, which comprises socks integral with said shell.

* * * * *

UNITED STATES PATENT AND TRADEMARK OFFICE
CERTIFICATE OF CORRECTION

PATENT NO. : 5,245,993

DATED : September 21, 1993

INVENTOR(S) : Michael B. McGrady and Michael W. Wright

It is certified that error appears in the above-identified patent and that said Letters Patent is hereby corrected as shown below:

Title page, under Section [57] Abstract, the 6th and 8th lines
   from the top, "shell (14)" should be -- shell (41) --.
Column 3, line 28, delete the comma after "to".
Column 4, line 1, delete the comma after "flap".
Column 4, line 41, delete the comma after "of".
Column 5, line 25, "Water" should be -- water --.
Column 5, line 56, delete the comma after "pictorial".
Column 8, line 59, delete the comma after "control".
Column 9, line 6, "5B'" should be -- 58' --.
Column 11, line 48, "see," should be -- see. --.
Column 12, line 50, there is a period after "aircraft".
Claim 10, column 14, line 59, "removable" should be
   -- removably --.
Claim 14, column 16, line 21, "claim 1" should be -- claim 11 --

Signed and Sealed this

Thirteenth Day of December, 1994

Attest:

BRUCE LEHMAN

Attesting Officer     Commissioner of Patents and Trademarks